(12) United States Patent
Pugh et al.

(10) Patent No.: US 9,158,127 B2
(45) Date of Patent: Oct. 13, 2015

(54) METHOD AND APPARATUS FOR A VARIABLE POWER OPHTHALMIC LENS

(71) Applicant: Johnson & Johnson Vision Care, Inc., Jacksonville, FL (US)

(72) Inventors: Randall B. Pugh, Jacksonville, FL (US); Daniel B. Otts, Fruit Cove, FL (US); James Daniel Riall, Saint Johns, FL (US); C. Benjamin Wooley, Jacksonville, FL (US); Edward R. Kernick, Jacksonville, FL (US); Frederick A. Flitsch, New Windsor, NY (US); Andres F. Arrubla, Washington, DC (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 58 days.

(21) Appl. No.: 13/854,853

(22) Filed: Apr. 1, 2013

(65) Prior Publication Data
US 2013/0258277 A1   Oct. 3, 2013

Related U.S. Application Data

(60) Provisional application No. 61/618,031, filed on Mar. 30, 2012.

(51) Int. Cl.
| | |
|---|---|
| *G02C 7/02* | (2006.01) |
| *G02C 7/04* | (2006.01) |
| *G02B 3/14* | (2006.01) |
| *G02B 26/00* | (2006.01) |
| *G02C 7/08* | (2006.01) |

(52) U.S. Cl.
CPC .. *G02C 7/02* (2013.01); *G02B 3/14* (2013.01); *G02B 26/005* (2013.01); *G02C 7/041* (2013.01); *G02C 7/083* (2013.01); *G02C 7/085* (2013.01)

(58) Field of Classification Search
CPC ............ G02C 7/02; G02C 7/04; G02C 7/041; G02C 7/06; G02B 3/12; G02B 3/14
USPC .......................... 351/159.03, 159.34, 159.39; 359/665–667

See application file for complete search history.

(56) References Cited

U.S. PATENT DOCUMENTS

| | | | |
|---|---|---|---|
| 8,355,209 B2 * | 1/2013 | Tsuji et al. ..................... 359/665 |
| 2006/0279848 A1 * | 12/2006 | Kuiper et al. .................. 359/666 |
| 2011/0157711 A1 | 6/2011 | Tsuji et al. |

(Continued)

FOREIGN PATENT DOCUMENTS

| | | |
|---|---|---|
| EP | 2085796 A1 | 8/2009 |
| EP | 2 108 983 A2 | 10/2009 |

(Continued)

OTHER PUBLICATIONS

EPO Search Report for EP 13 16 1793, Date of mailing Jul. 2, 2013.

(Continued)

*Primary Examiner* — Darryl J Collins (57) ABSTRACT

This invention discloses methods and apparatus for providing an ophthalmic lens with diffractive/refractive variable optic structures. An energy source is capable of powering the variable optic included within the ophthalmic lens as it may be predetermined. In some embodiments, an ophthalmic lens is cast molded from a silicone hydrogel.

28 Claims, 9 Drawing Sheets

(56) References Cited

U.S. PATENT DOCUMENTS

2011/0279905 A1* 11/2011 Pugh et al. .................... 359/665
2012/0075710 A1    3/2012 Pugh et al.

FOREIGN PATENT DOCUMENTS

| JP | 2007225779 A | 9/2008 |
| WO | WO 2005003843 A1 | 1/2005 |
| WO | WO 2005006029 A1 | 1/2005 |
| WO | WO 2005088388 A1 | 9/2005 |
| WO | WO 2005088610 A2 | 9/2005 |
| WO | WO 2006100624 A2 | 2/2006 |
| WO | WO 2008062067 A1 | 5/2008 |
| WO | WO 2010076473 A1 | 7/2010 |
| WO | WO 2011143554 A1 | 11/2011 |
| WO | WO 2012005922 A1 | 1/2012 |

OTHER PUBLICATIONS

Singapore Search Report for Corresponding Application No. 201302365-0 dated Jul. 18, 2014.

* cited by examiner

PLACE A VARIABLE OPTIC PORTION WITH AN ENERGY SOURCE WITHIN AN OPHTHALMIC LENS

501

PLACE THE ENERGY SOURCE IN ELECTRICAL COMMUNICATION WITH THE VARIABLE OPTIC PORTION

502

DIRECT ELECTRICAL CURRENT THROUGH THE VARIABLE OPTIC PORTION

503

CHANGE AT LEAST ONE OPTICAL CHARACTERISTIC OF THE LENS

METHOD AND APPARATUS FOR A VARIABLE POWER OPHTHALMIC LENS

CROSS REFERENCE TO RELATED APPLICATIONS

This application claims priority to the U.S. Provisional Application No. 61/618,031, filed Mar. 30, 2012, the contents of which are relied upon and incorporated herein.

FIELD OF USE

The present invention relates generally to an Arcuate ophthalmic lens, more specifically, where the ophthalmic lens of this invention can include a series of Concentric Annular Sections. Said Concentric Annular Sections comprising variable liquid meniscuses in between a front curve Arcuate optical defining surface and a back curve Arcuate defining surface to provide a thinner variable power ophthalmic lens.

BACKGROUND OF THE INVENTION

Liquid meniscus lenses have been known in various industries. As discussed more fully below with reference to FIGS. 1A and 1B, known liquid meniscus lenses were engineered in cylindrical shapes with a perimeter surface formed by points at a fixed distance from an axis which is a straight line. Known examples of the use of liquid meniscus lenses include devices such as electronic cameras and mobile phone devices.

Traditionally, an ophthalmic device, such as a contact lens and an intraocular lens include one or more biocompatible device(s) with corrective, cosmetic, or therapeutic functionality. A contact lens, for example, can provide one or more of: vision correcting functionality; cosmetic enhancement; and therapeutic effects. Each function provided by a physical characteristic of the lens. For example, a design incorporating a refractive quality into a lens can provide a vision corrective function, a pigment incorporated into the lens can provide a cosmetic enhancement, and an active agent incorporated into a lens can provide a therapeutic functionality.

More recently, a contact lens taught by the inventor in referenced applications can include an Arcuate liquid meniscus lens with a single Meniscus Wall and physical features conducive to one or both of attraction and repulsion of a liquid contained within the lens and forming a meniscus boundary with another liquid. Such lenses include a first optic proximate to a second optic with a cavity formed therebetween. A saline solution and an oil are maintained within the cavity. Application of an electrical charge to a Meniscus Wall generally located in a perimeter area of one or both of the first optic and the second optic changes the physical shape of a meniscus formed between the saline solution and oil maintained within the cavity thereby changing the power of the lens. However, some of these designs may suffer from limitations in some applications.

Consequently, what is needed are additional ophthalmic lens designs that can exploit the advantages of both diffractive and refractive variable optical structures for vision correction.

SUMMARY OF THE INVENTION

Accordingly, the present invention provides a variable power ophthalmic Lens with physical and chemical features conducive for inclusion in an ophthalmic lens, for example a contact lens or an intraocular lens. More specifically, where the ophthalmic Lens can exploit properties of both diffractive and refractive variable optical structures.

According to the present invention, a first Arcuate shaped Optic defining surface is proximate to a second Arcuate Shaped Optic defining surface forming a Lens Cavity therebetween. A saline solution and an oil are maintained within the cavity. Application of electrical charge to at least one predetermined region of one or both of the first Arcuate optic defining surface and the second Arcuate optic defining surface can form or change the physical shape, in discrete steps, of a series of optical Concentric Annular Sections. Said optical Concentric Annular Sections which can be formed or changed using an electric current via techniques such as, for example Electrowetting or Electrophoresis, to define liquid meniscuses between the saline solution and oil maintained within the cavity.

The physical change of the liquid meniscuses may form or vary optical structures as it may be predetermined to thereby provide variable optical characteristics which can provide for a change in focal length and allow for thinner Arcuate ophthalmic Lenses. Said Arcuate ophthalmic Lenses which respond providing one or both diffractive and refractive variable optical structures at different states.

DETAILED DESCRIPTION OF THE INVENTION

The present invention provides for an ophthalmic lens with physical and chemical features conducive for inclusion in an ophthalmic lens, such as a contact lens or an intraocular lens. In the following sections detailed descriptions of embodiments of the invention will be given. The description of both preferred and alternative embodiments though are exemplary embodiments only, and it is understood that to those skilled in the art that variations, modifications, and alterations may be apparent. It is therefore to be understood that the exemplary embodiments do not limit the broadness of the aspects of the underlying invention as defined by the claims.

GLOSSARY

In this description and claims directed to the presented invention, various terms may be used for which the following definitions will apply:

"Arcuate" as used herein, refers to a curve or bend like a bow shape.

"Concentric Annular Sections" as used herein, refers to one or more formed ring or spiral shaped optical structures having a common center. For example, a series of ring shaped sections in the optical zone of an ophthalmic lens that may result in a diffractive lens which alters the power and the aberrations of the ophthalmic lens.

"Contact Angle" as used herein, refers to the angle at which the oil/saline solution interface, also referred to as the Liquid Meniscus Boundary, meets the Meniscus Wall. In the case of a linear Meniscus Wall, the contact angle is measured as the angle between the Meniscus Wall and the line tangent to the Liquid Meniscus Boundary at the point where the Liquid Meniscus Boundary meets the Meniscus Wall. In the case of a curved Meniscus Wall, the contact angle is measured as the angle between the lines tangent to the Meniscus Wall and the Liquid Meniscus Boundary at the point where they meet.

"Energized" as used herein, refers to the state of being able to supply electrical current to or have electrical energy stored within.

"Energy" as used herein, refers to the capacity of a physical system to do work. Many used within this invention may relate to the said capacity being able to perform electrical actions in doing work.

"Energy Source" as used herein, refers to the device capable of supplying Energy or placing a biomedical device in an Energized state.

"Lens" as used herein, refers to an article with a front surface and a back surface that is optically transmissive to a predefined range of wavelengths of radiation, such as, by way of example, visible light. A lens may include one or both of a front surface and a back surface which are essentially flat or one or both of a front surface and a back surface which are Arcuate in shape. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision.

"Lens Cavity" as used herein, refers to the space in an Arcuate liquid meniscus lens between the front curve defining surface and the back curve defining surface in which oil and saline solution are maintained.

"Liquid Meniscus Boundary" as used herein, refers to one or more Arcuate surface interface(s) between the saline solution and the oil. For example, the surface can form one or more lens that is concave on one side and convex on the other.

"Lithium Ion Cell" as used herein, refers to an electrochemical cell where Lithium ions move through the cell to generate electrical energy. This electrochemical cell, typically called a battery, may be reenergized or recharged in its typical forms.

"Media Insert" as used herein, refers to a formable or rigid substrate capable of supporting an Energy Source within an ophthalmic lens. In some embodiments, the Media Insert also includes one or more variable optic lenses.

"Meniscus Wall" as used herein, refers to a specific area on the interior of the front curve lens, such that it is within the meniscus cavity, along which the liquid meniscus boundary moves.

"Mold" as used herein, refers to a rigid or semi-rigid object that may be shaped to aid in the defining of physical properties of the diffractive structures. The Mold may also be one or both of the front curve or back curve defining surface(s) of the Lens.

"Optical Zone" as used herein, refers to an area of a lens through which a user of the lens sees through. For example, the area in a ophthalmic lens through which a wearer of the ophthalmic lens sees "Power" as used herein, refers to work done or energy transferred per unit of time.

"Rechargeable" or "Re-energizable" as used herein, refers to a capability of being restored to a state with higher capacity to do work. Many uses within this invention may relate to the capability of being restored with the ability to flow electrical current at a certain, reestablished time period.

"Reenergize" or "Recharge" as used herein, refers to the restoration of an Energy Source to a state with higher capacity to do work. Many uses within this invention may relate to restoring a device to the capability to flow electrical current at a certain rate for a certain, reestablished period.

"Sharp" as used herein, refers to a geometric feature of an internal surface of either a front curve or back curve lens defining surface sufficient to contain the location of a contact line of two predefined fluids on the optic. The Sharp is usually an outside corner rather than an inside corner. From a fluid standpoint can be an angle greater than 180 degrees.

"Substrate" as used herein, refers to a physical entity upon which other entities are placed or formed.

"Variable Optic" as used herein, refers to the capacity to change an optical quality, such as for example the optical structure of a lens.

DESCRIPTION

The present invention provides for an ophthalmic device with at least one of a front curve defining surface and a back curve defining surface to provide a Lens Cavity, wherein a series of Concentric Annual Sections can be formed, changed, or maintained to thereby provide for optical structures that may be capable of changing physical characteristics. The physical characteristics of the Concentric Annual Sections and overall shape of the ophthalmic lens which may be designed and internally controlled to provide an improved ophthalmic Lens with both refractive and diffractive properties.

Figure 1A:
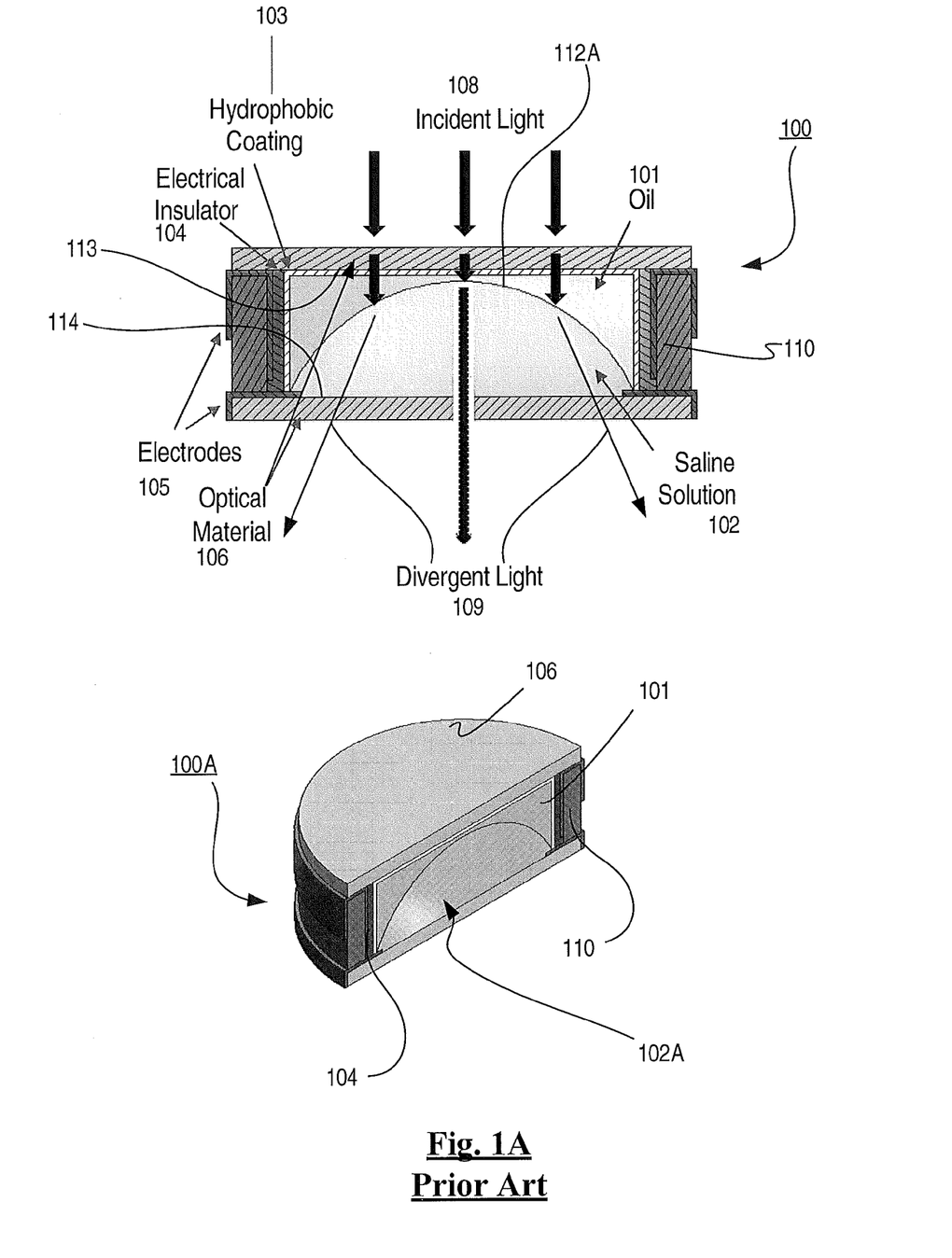
FIG. 1A illustrates a prior art example of a cylindrical liquid meniscus lens in a first state.

Referring now to FIG. 1A, a cut away view of a prior art lens 100 is illustrated with an oil 101 and a saline solution 102 contained within a cylinder 110. The cylinder 110 includes two plates of optical material 106. Each plate 106 includes a flat interior surface 113-114. The cylinder 110 includes an interior surface that is essentially rotationally symmetric. In some prior art embodiments, one or more surfaces may include a hydrophobic coating. Electrodes 105 are also included on or about the perimeter of the cylinder. An electrical insulator 104 may also be used proximate to the electrodes 105.

According to the prior art, each of the interior surfaces 113-114 is essentially flat or planar. An interface surface 112A is defined between the saline solution 102 and the oil 101. As illustrated in FIG. 1A, the shape of the interface 112A is combined with the refractive index properties of the saline solution 102A and the oil 101 to receive incident light 108 through a first interior surface 113 and provide divergent light 109 through a second interior surface 114 if the index of refraction of the oil is greater than the index of refraction of the saline. The shape of the interface surface between the oil 101 and the saline solution 102 may be altered with the application of an electrical current to the electrodes 105.

At 100A, a perspective view of the prior art lens illustrated at 100 is illustrated.

Figure 1B:
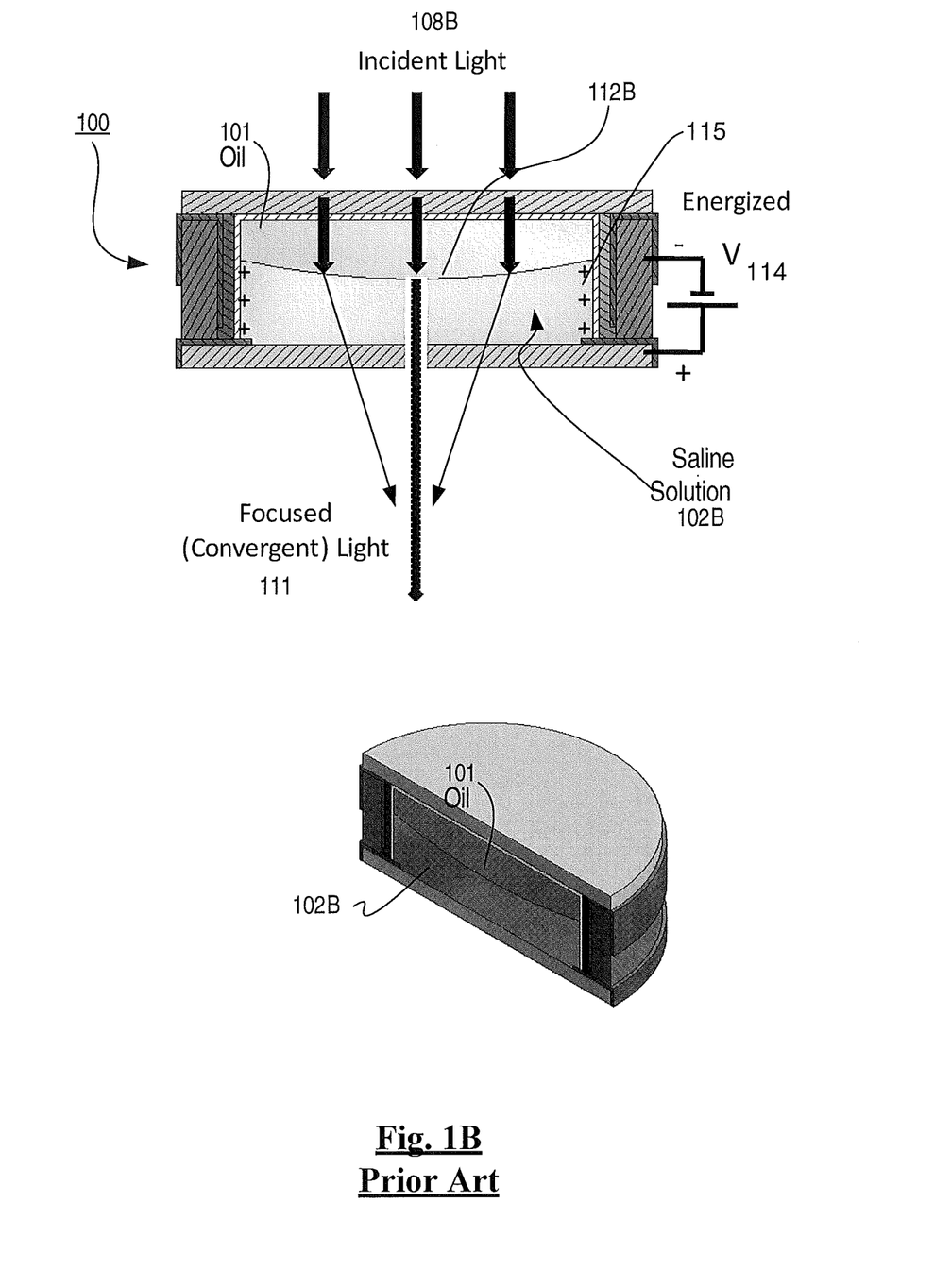
FIG. 1B illustrates the prior art example of a cylindrical liquid meniscus lens in a second state.

Referring now to FIG. 1B, the prior art lens 100 is illustrated in an energized state. The energized state is accomplished by applying voltage 114B across the electrodes 105. The shape of the interface surface 112B between the oil 101 and the saline solution 102 is altered with the application of an electrical current to the electrodes 105. As illustrated in FIG. 1B, incident light 108 passing through the oil 101 and the saline solution 102 is focused into a convergent light pattern 111B.

In other filed application disclosures by the same inventor, it was taught that in some embodiments that are generally Arcuate in shape, through Meniscus Wall manipulations, use of one or more Sharp(s) in one or more Meniscus Wall(s), Power control, etc. the physical properties of the liquid meniscus could be changed and controlled. Exploiting the advantages of the disclosed control parameters and designs, other embodiments were realized and are now described herein to provide for novel lenses that may be significantly thinner and/or more powerful, the subject matter of the present invention.

In the present invention, thinner ophthalmic lenses can result using an internally controlled series of Concentric Annular Sections formed by liquid meniscuses that are formed into a structure that repeats radially with either increasing or decreasing radial sizes to form a diffractive optical element or diffractive lens. A key feature of a diffractive lens is that the focusing power can be achieved with a thin structure, with the total height of the structure being on the order of $\lambda/\Delta n$ where $\lambda$ is the wavelength of light (~550 nm) and $\Delta n$ is the change in index of refraction across the interface.

Figure 2A:
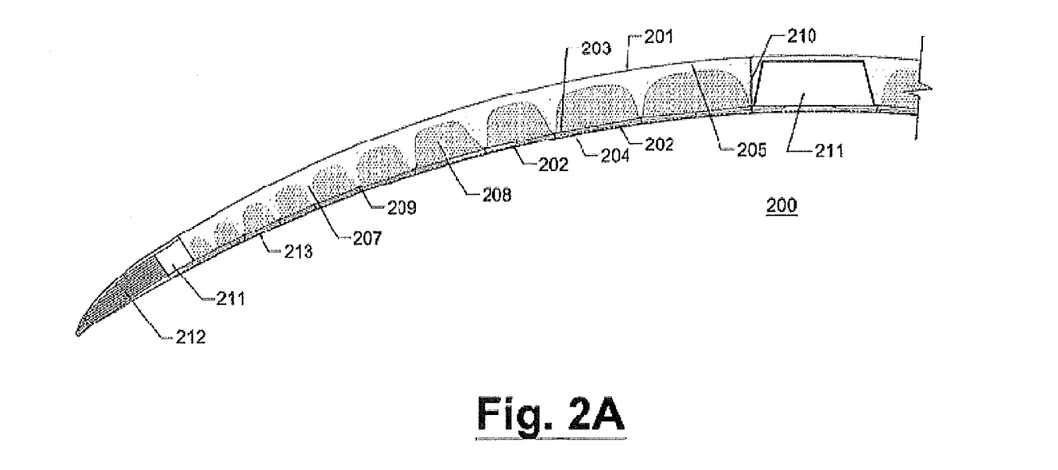
FIG. 2A illustrates a cross section of an exemplary ophthalmic lens in an energized state according to some embodiments of the present invention.

Referring now to FIG. 2A, a cross section of an exemplary ophthalmic lens according to some embodiments of the present invention is depicted in an Energized state. At 200, a cross section of an Arcuate lens with a front curve defining surface 201 and a back curve defining surface 202 is depicted. Each of said front curve and back curve defining surfaces which may be made up of a rigid optical material that is at least partially transmissive to light. In some embodiments, the front curve lens 201 and the back curve lens 202 may be positioned proximate to each other and form a cavity 210 therebetween.

In some embodiments, the back curve lens 202 includes a convex Arcuate interior lens surface 203 and a concave Arcuate exterior lens surface 204. The convex Arcuate lens surface 203 may have one or more coatings (not illustrated in FIG. 2A). Coatings may include, for example, one or more of electrically conductive materials or electrically insulating materials, hydrophobic materials or hydrophilic materials. One or both of the Arcuate lens surface 203 and the coatings may be in liquid and optical communication with an oil 208 contained within the cavity 210.

The front curve optical defining surface 201 may include a concave Arcuate interior lens surface 205 and a convex Arcuate exterior lens surface 206. The concave Arcuate lens surface 205 may have one or more coatings (not illustrated in FIG. 2). Coatings may include, for example, one or more of electrically conductive materials or electrically insulating materials, hydrophobic materials or hydrophilic materials. At least one of the concave Arcuate lens surface 205 and the coatings are in liquid and optical communication with a saline solution 207 contained within the cavity 210. The saline solution 207 can include one or more salts or other components which are electrically conductive and as such may be either attracted to or repulsed by an electric charge using Electrowetting or Electrophoresis techniques.

According to the present invention, the Lens may be Energized and accordingly can further comprise an electrically conductive coating 209 which may be located along at least a portion of a periphery of one or both of the front curve lens 201 and the back curve lens 202. The electrically conductive coating 209 may include gold or silver and is preferably biocompatible. Application of an electrical charge to the electrically conductive coating 209 may cause a change in contact angle or either an attraction or a repulsion of the electrically conductive salts or other components in the saline solution as it may be predetermined.

In some embodiments, the front and back curve lenses 201, 202 may have optical powers in relation to the light refracting through the either or both the Arcuate interior lens surfaces and the Arcuate exterior lens surfaces 203-206. The optical power may be 0 diopters or may be a plus or minus power. In some preferred embodiments, the optical power is a power typically found in corrective contact lenses, such as, by way of non-limiting example, a power between −8.0 and +8.0 diopters.

Additionally, when the lens is energized as depicted in this exemplary embodiment, Concentric Annular Sections of liquid meniscuses may be formed, as it may be predetermined, to enable additional diffractive physical properties. This which may allow the Optical Zone of the Lens to function as a Variable Optic in discrete steps.

Accordingly, the optical power of the Lens may be controlled by design parameters such as: angle of curvature of each defining surface and the refractive index of the defining surfaces of the device and the saline/oil, the contact angle and chemical properties of the saline and oil in the lens cavity, the voltage applied to the zones comprising the electric coating, and the physical characteristics of the predetermined Concentric Annular Sections of the Lens.

Diffractive Lenses diffract the incident light into multiple orders. Each order has a different power. The diffraction efficiency into the various orders is controlled by the shape of the structure within each concentric annular section to provide high diffraction efficiency into the power(s) of interest when the device is in the energized (diffractive lens "on") state.

In some diffractive embodiments the innermost Concentric Annular Section being the center of the Lens and may be aligned with the pupil. Because of large depth of field of the lens within this small central pupil, any structure on the innermost Concentric Annular Section may not have a dramatic negative effect on the optical properties of the Lens. Consequently, in some embodiments an integrated reservoir 211 for the oil 208 may be placed there and along the edges of the ophthalmic device, with the electronics/power source 212, where vision of a user may not be significantly affected.

Figure 2B:
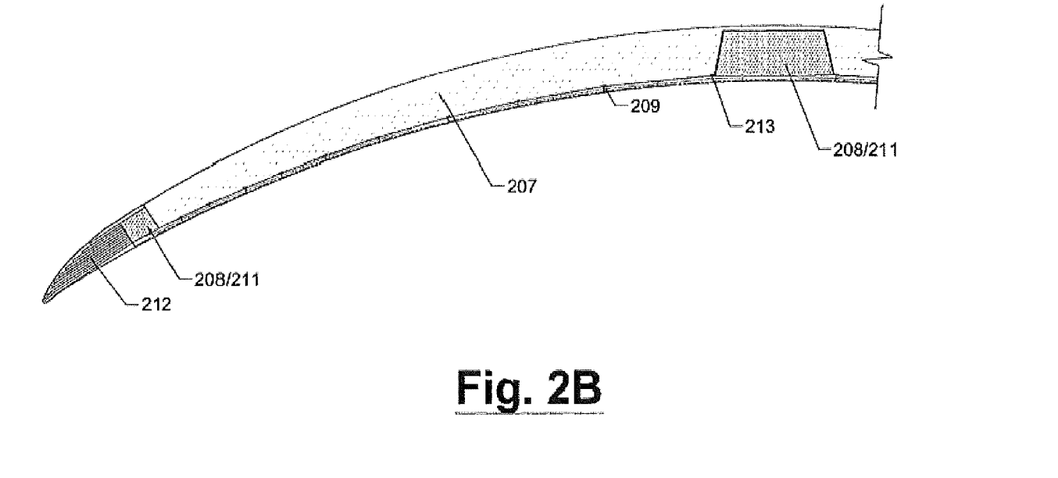
FIG. 2B illustrates a cross section of an exemplary ophthalmic lens in a de-energized state according to some embodiments of the present invention.

Referring now to FIG. 2B, the cross section described in FIG. 2A is depicted in a de-energized state. In this state, the liquid meniscus diffractive structures are non-existing thereby providing a different power than the one provided by the energized state (i.e. the power of the diffractive physical properties). The oil 208 may be contained in the oil reservoirs 211 as described above. In some embodiments, the saline may be indexed matched to the defining surfaces to provide, when de-energized, the refractive power desired of the Arcuate shape and optical lens material. The oil may flow through energized channels 213 that may cause the oil to flow to the reservoirs 211. Accordingly, in some embodiments the energized channels 213 may function as a pumping device depending on the power and the electrochemical characteristics of the saline 207/oil 208.

In other embodiments, one or both of said Lens defining surfaces may comprise optical quality molded regions with electrical conductors to change the properties of the oil and saline, as it may be predetermined. Different variations of the molded parts, material's of the defining surfaces, saline and oil and more specifically their respective diffractive index and contact angles may be possible to create a variable optical power Lens with refractive and diffractive properties without having to displace the oil to reservoirs as in the first exemplary embodiment.

Figure 3A:
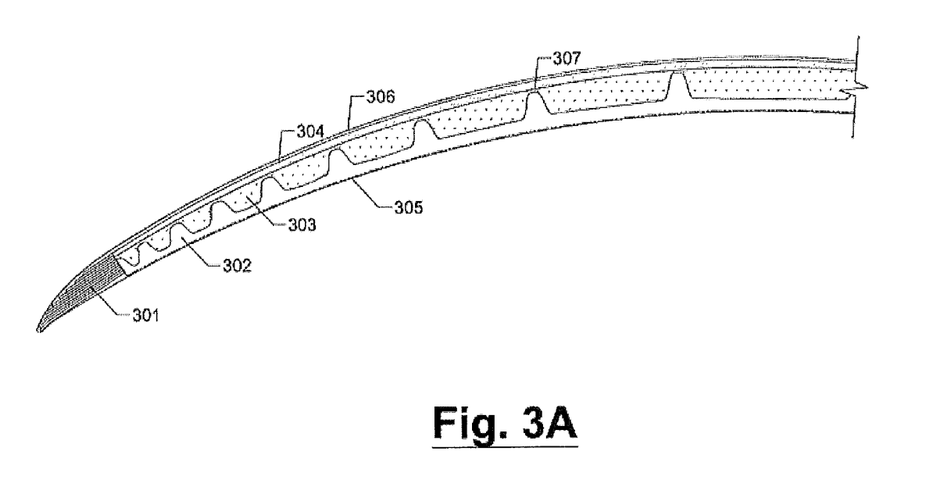
FIG. 3A illustrates a cross section of another exemplary ophthalmic lens in an energized state according to some embodiments of the present invention.

Referring now to FIG. 3A, a cross section of another exemplary ophthalmic lens that uses a molded optical defining surface in an energized state is depicted. At 305, the back curve optical defining surface of the Lens includes at least a molded portion 302 that may contain a significant amount of oil in different sections within the Lens cavity when the lens is not energized (shown in FIG. 3B). To the contrary, when the indexed matched oil with the molded structure may cover the diffractive optical structures of the mold, the diffractive optical properties of the lens are passive and may not have an effect. (In other embodiments, the molded defining surface may include either the front defining surface 306 or both the back defining surface 305 and the front defining surface 306.) Furthermore, the molded portion 302 can include a series of diffractive structures 307 that may additionally serve as meniscus walls that can support conductors of electricity for the implementation of Electrowetting or Electrophoresis techniques.

Figure 3B:
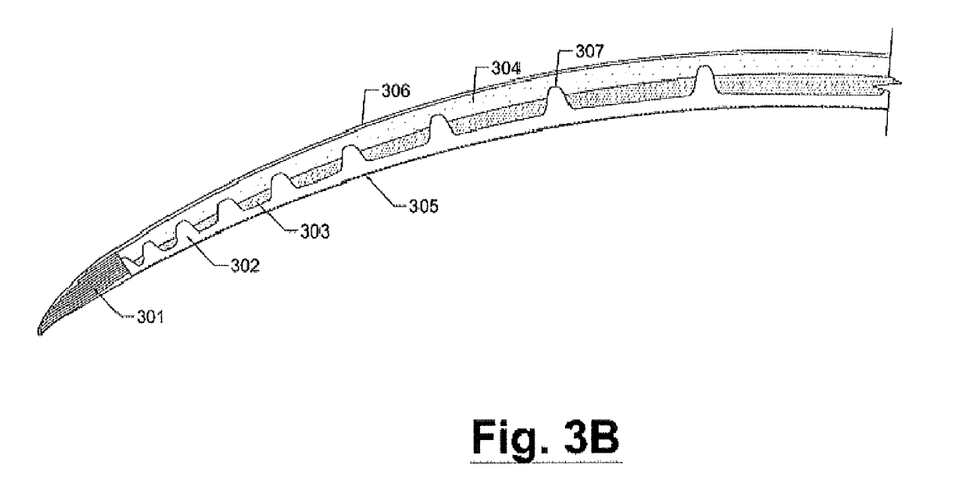
FIG. 3B illustrates a cross section of another exemplary ophthalmic lens in a de-energized state according to some embodiments of the present invention.

In this exemplary embodiment, the walls may be energized to cause the volume of oil 303 to cover the diffractive structures, for example the peaks shown in 307 in FIG. 3A. Further, as it may be apparent to someone skilled in the art, the spacing of the diffractive structures along the Lens may be closer to each other to design a higher efficiency Lens, i.e. higher power and aberration correction. Because the saline solution and the mold may have a different refractive index, light would be diffracted as it may be predetermined when the diffractive properties are exposed to the saline solution as depicted in FIG. 3B where the lens is de-energized. In this de-energized estate, the mold diffractive structures 307 are uncovered. When uncovered the index of refraction changes at those portions thereby providing a lens that may provide both refractive and diffractive characteristics.

As depicted in FIG. 3A and in FIG. 3B, the saline solution 304 used may be displaced by the oil when energized or de-energized in other embodiments. Integrated circuits, sensors, batteries and other non-optical components may be included in the outer diameter (edges) 301 of the lens where the vision of the user may not be significantly affected.

Figure 4:
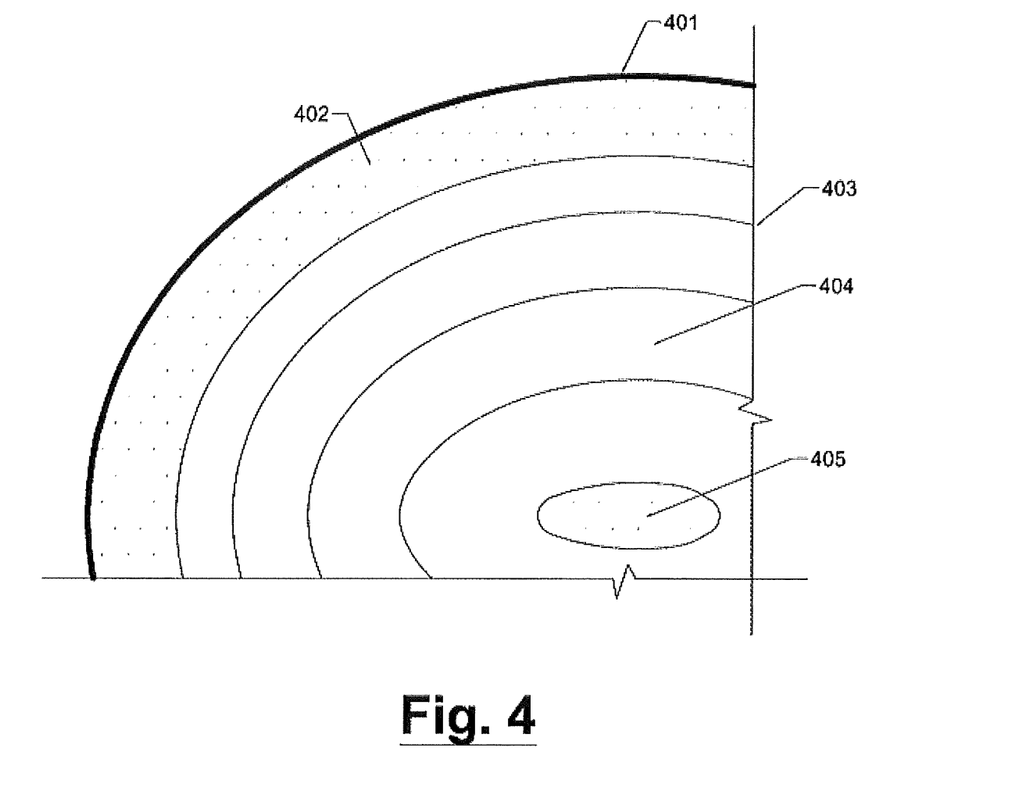
FIG. 4 illustrates an exemplary top view section of the exemplary embodiments presented in FIGS. 2A-3B.

Referring now to FIG. 4, an exemplary top view section of the exemplary embodiments presented in FIGS. 2A-3B is depicted. At 401, the edge of the lens is shown. At 402, an outer edge portion of the lens is depicted wherein the electronics, pumps, reservoirs and any non-optical components of the lens may be placed without significantly affecting the vision of the user. At 403-405, an exemplary concentric spiral pattern is shown for the conductive material used for the diffractive structure to be energized.

In some embodiments, the pattern may be important to control the voltage of each lens or specified regions as it may be desired. For example, to resemble a Fresnel lens and obtain the refractive properties of it, in some embodiments where diffractive structures comprise liquid meniscuses formed by energizing predetermined regions, it is important that all diffractive structures be significantly aligned, one way of achieving this is to consider the pinning effect and amount of current directed towards each predetermined region. Consequently, some predetermined regions may require more power to provide for the added volume of oil to form the diffractive structure as it may be designed to correct specific aberrations/provide optimal optic power. As a result, the charge can be applied so that it travels in concentric circles to the center decreasing progressively to align the height of the meniscuses of the oil.

At 405, in embodiments such as the one depicted in FIGS. 2A and 2B this center portion of the lens is used as a reservoir. A variety of variations are possible and depend on the desired design of the lens. However, it is most important, as it may be apparent to those skilled in the art after reading this disclosure that by forming and/or controlling diffractive optical structures that resemble the Fresnel lens, a functional Lens with variable optical structures may be designed. Moreover, the variable optical power lens may incorporate a controller and a source of power in its design to be autonomous in the process.

Although the invention may be used to provide hard or soft contact lenses made of any known lens material, or material suitable for manufacturing such lenses, preferably, the lenses of the invention are soft contact lenses having water contents of about 0 to about 90 percent. More preferably, the lenses are made of monomers containing hydroxy groups, carboxyl groups, or both, or are made from silicone-containing polymers, such as siloxanes, hydrogels, silicone hydrogels, and combinations thereof. Material useful for forming the lenses of the invention may be made by reacting blends of macromers, monomers, and combinations thereof along with additives such as polymerization initiators. Suitable materials include, without limitation, silicone hydrogels made from silicone macromers and hydrophilic monomers.

Figure 5:
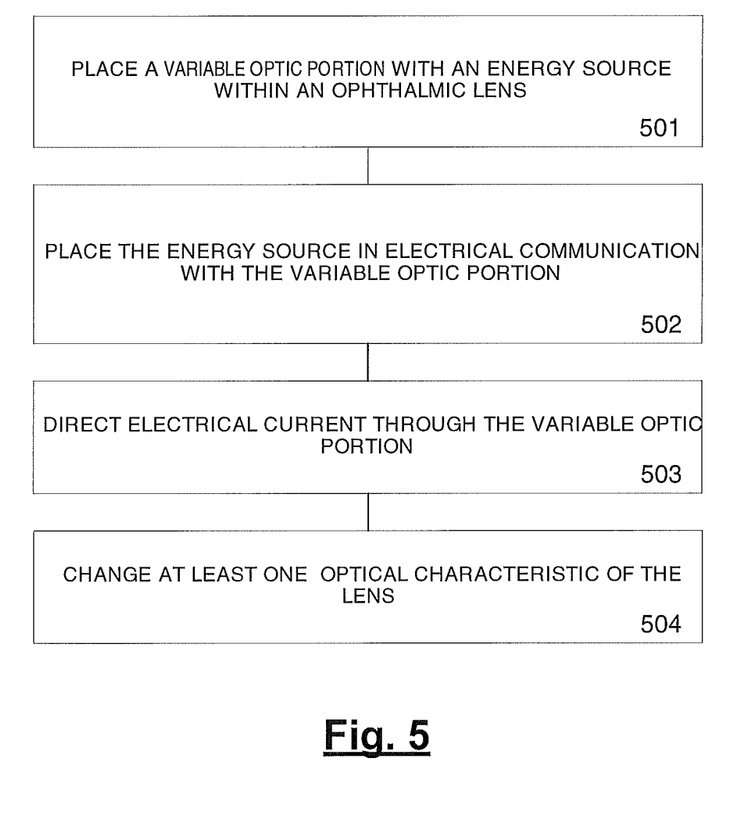
FIG. 5 illustrates method steps that may be implemented for some embodiments of the present invention.

Referring now to FIG. 5, method steps that may be implemented for some embodiments of the present invention are illustrated. These method steps described are listed in a logical sequence in this discussion. However, this sequence by no means limits the order in which they may be implemented unless specifically stated.

At 501, a Variable Optic portion is placed within an ophthalmic lens, as discussed above. At 502, the Variable Optic portion is placed in electrical communication with an Energy Source. Electrical communication can be accomplished, for example, via circuitry incorporated into the variable optic portion or via pathways ink jetted or otherwise formed directly upon lens material.

At 503, electrical energy is directed through predetermined sections of the variable optic portion in the Lens. The energy can be directed, for example, via electrical circuitry capable of conducting the electrical charge. At 504 the variable optic can change at least one optical quality structure of the lens as previously described to be able of providing different optical power at discrete steps.

Figure 6:
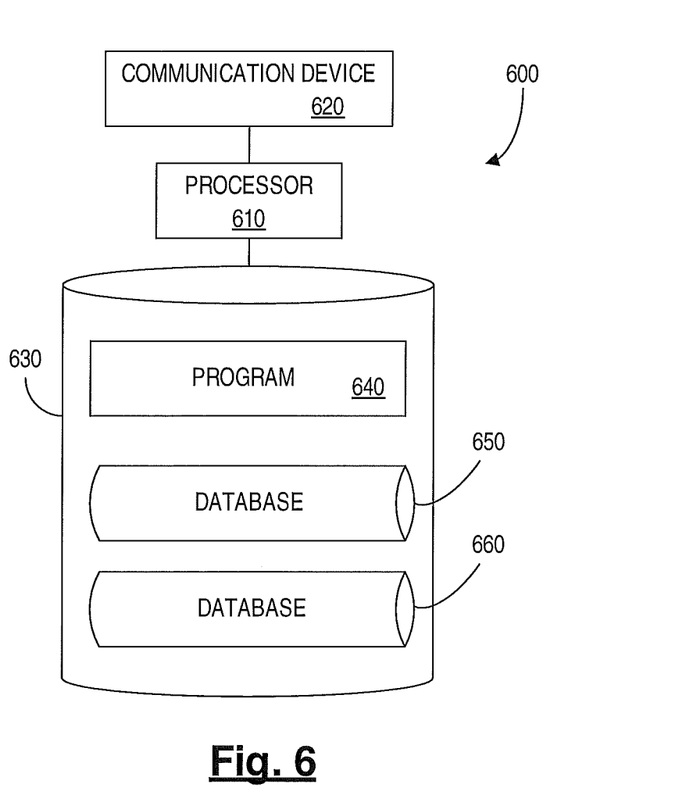
FIG. 6 illustrates a processor that may be used to implement some embodiments of the present invention.

Referring now to FIG. 6, a controller 600 is illustrated that may be used in some embodiments of the present invention. The controller 600 includes a processor 610, which may include one or more processor components coupled to a communication device 620. In some embodiments, a controller 600 can be used to transmit energy to the Energy Source placed in the ophthalmic lens.

The controller can include one or more processors, coupled to a communication device configured to communicate energy via a communication channel. The communication device may be used to electronically control one or more of: the placement of an variable optic insert into the ophthalmic lens and the transfer of a command to operate a Variable Optic device.

The communication device 620 may also be used to communicate, for example, with one or more controller apparatus or manufacturing equipment components.

The processor 610 is also in communication with a storage device 630. The storage device 630 may comprise any appropriate information storage device, including combinations of magnetic storage devices, optical storage devices, and/or semiconductor memory devices such as Random Access Memory (RAM) devices and Read Only Memory (ROM) devices.

The storage device 630 can store a program 640 for controlling the processor 610. The processor 610 performs instructions of the program 640, and thereby operates in accordance with the present invention. For example, the processor 610 may receive information descriptive of variable optic insert placement, processing device placement, and the like. The storage device 630 can also store ophthalmic related data in one or more databases 650, 660. The database 650,660 may include specific control logic for controlling energy to and from a Variable Optic lens.

CONCLUSION

The present invention, as described above and as further defined by the claims below, provides methods of providing an ophthalmic lens with a variable optic portion. The variable optic portion which may vary to provide diffractive and/or refractive properties as it may be predetermined.

The invention claimed is:

1. An optical lens comprising:
    a front curve optic defining surface;
    a back curve optic defining surface, wherein both said optic defining surfaces comprise anarcuate shape and are positioned proximate to each other forming a cavity therebetween;
    a conductive coating on at least one portion of one or both of said defining surfaces contiguous to the cavity; and
    a volume of oil and a volume of saline solution within said cavity, wherein the oil and saline solution provide a series of meniscus boundaries which each define internally controlled concentric annular rings with variable optical structures, upon the application of an electrical charge to said conductive coating.

2. The optical lens of claim 1, wherein the application of the electrical charge changes the variable optical structures of the optical lens via Electrowetting techniques.

3. The optical lens of claim 1, wherein the application of the electrical charge changes the variable optical structures of the optical lens via Electrophoresis techniques.

4. The optical lens of claim 1, wherein the variable optical structures are capable of providing the optical lens with variable optical powers at discrete steps.

5. The optical lens of claim 1, wherein the volume of oil is from 65% to 90% of the volume of saline solution.

6. The optical lens of claim 1, wherein the oil has a density within about 5% of a density of the saline solution.

7. The optical lens of claim 1, wherein at least a portion of the conductive coating extends from an area interior to the cavity to an area external to the cavity.

8. The optical lens of claim 7, wherein the area of conductive coating external to the cavity forms an electrical terminal for providing the electrical charge to the variable optical structures.

9. The optical lens of claim 8, the application of the electrical charge to the area of conductive coating external to the cavity causes a change in the shape of the meniscuses.

10. The optical lens of claim 1, wherein the electrical charge comprises a direct current.

11. The optical lens of claim 10, wherein the direct current comprises from 3.5 to 22 volts.

12. The optical lens of claim 1, wherein the front curve optic defining surface comprises an optical power other than 0.

13. The optical lens of claim 1, wherein the back curve optic defining surface comprises an optical power other than 0.

14. The optical lens of claim 1, additionally comprising a channel through one or both of the optic defining surfaces.

15. The optical lens of claim 14, additionally comprising a conductive material inside the channel.

16. The optical lens of claim 15, additionally comprising a terminal in electrical communication with the conductive material inside the channel.

17. The optical lens of claim 16, wherein the application of the electrical charge to the terminal causes a change in the shape of the variable optical structures.

18. The optical lens of claim 15, additionally comprising a first fluid reservoir at the peripheral edge of the optical lens.

19. The optical lens of claim 18, wherein an inner most concentric annular section comprises a second fluid reservoir.

20. The optical lens of claim 19, wherein the oil may flow between the first fluid reservoir, the variable optical structures and the second fluid reservoir.

21. The optical lens of claim 1, additionally comprising an insulator coating along at least a portion of the front curve optic defining surface, wherein the insulator coating comprises an electrical insulator.

22. The optical lens of claim 21, wherein the electrical insulator comprises Parylene C.

23. The optical lens of claim 22, wherein the electrical insulator comprises Teflon AF.

24. The optical lens of claim 21, wherein the electrical insulator comprises a boundary area to maintain separation between the conductive coating and the saline solution contained in the cavity.

25. The optical lens of claim 1, wherein an innermost concentric annular section comprises a functional component.

26. The optical lens of claim 25, wherein the functional component includes a reservoir for a liquid.

27. The optical lens of claim 1, wherein the concentric annular sections repeat radially with either increasing or decreasing radial sizes.

28. An optical lens comprising:
    a front curve optic defining surface;
    a back curve optic defining surface;
    a conductive coating on at least a portion of one or both of the optic defining surfaces;
    a volume of oil; and
    a volume of saline solution,
    wherein both optic defining surfaces comprise an arcuate shape and are positioned proximate to each other forming a cavity therebetween,
    wherein the oil and the saline solution are disposed within said cavity, and
    wherein an application of an electrical charge to said conductive coating causes the oil and the saline solution to form a series of meniscuses in concentric annular sections with different optical properties.

* * * * *